Figure 1:
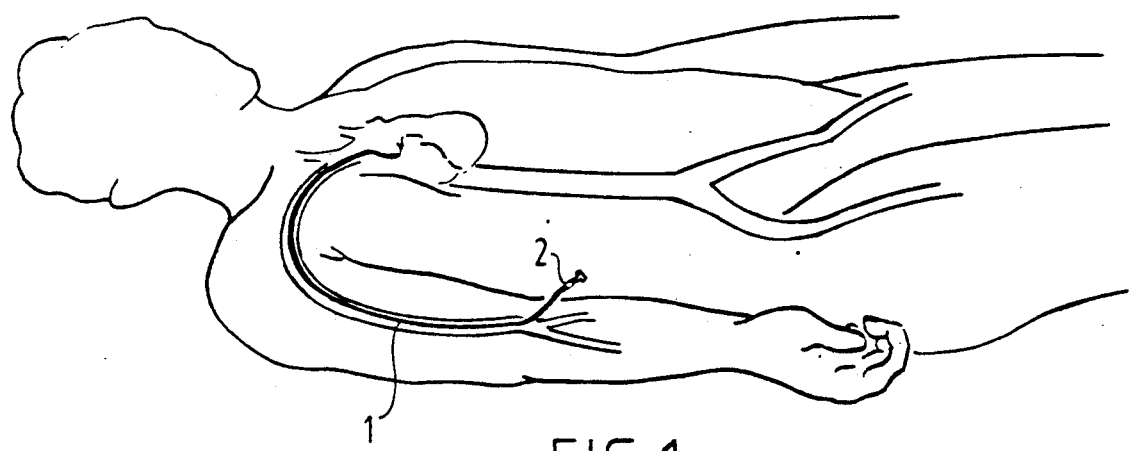

United States Patent [19]

Deuss

[11] Patent Number: 5,122,125
[45] Date of Patent: Jun. 16, 1992

[54] CATHETER FOR ANGIOPLASTY WITH SOFT CENTERING TIP

[75] Inventor: Jacobus A. C. Deuss, Son en Breugel, Netherlands

[73] Assignee: Ashridge A.G., Zug, Switzerland

[21] Appl. No.: 514,213

[22] Filed: Apr. 25, 1990

[51] Int. Cl.⁵ ............................................. A61M 25/00
[52] U.S. Cl. ................................. 604/282; 604/280
[58] Field of Search ................................... 604/52-53, 604/280-281, 95, 104, 264, 282-283; 606/191-192, 198; 128/658, 657; 138/109

[56] References Cited

U.S. PATENT DOCUMENTS

| | | | |
|---|---|---|---|
| 1,626,839 | 5/1927 | Kallmeyer | 604/264 |
| 4,405,313 | 9/1983 | Sisley | 604/53 |
| 4,563,181 | 1/1986 | Wijayarathna | 604/280 |
| 4,571,240 | 2/1986 | Simpson | 604/96 |
| 4,573,476 | 3/1986 | Ruiz | 604/280 |
| 4,636,346 | 1/1987 | Gold et al. | 604/280 |
| 4,735,620 | 4/1988 | Ruiz | 604/281 |
| 4,737,153 | 4/1988 | Shimamura et al. | 604/282 |
| 4,863,442 | 9/1989 | DeMello | 604/282 |
| 4,886,506 | 12/1989 | Lovgren | 604/280 |
| 4,961,731 | 10/1990 | Bodicky et al. | 604/280 |
| 4,983,165 | 1/1991 | Loiterman | 604/101 |
| 5,045,072 | 9/1991 | Castillo et al. | 604/280 |
| 5,054,500 | 10/1991 | Littleford et al. | 604/96 |

*Primary Examiner*—C. Fred Rosenbaum
*Assistant Examiner*—Mark Bockelman
*Attorney, Agent, or Firm*—Wegner, Cantor, Mueller & Player

[57] ABSTRACT

Guiding catheter for angioplasty, substantially consisting of a hollow tube (lumen) of flexible torsion-stiff material, onto an end of which connects a tubular extension of flexible material, which is curved according to predetermined varying radii of curvature, and the free end portion of which is provided with a softer material than the flexible material, wherein the end portion of softer material is provided with at least three radially protruding elements, preferably having an arc-like outer curvature seen in tangential direction. A very great stability of the end portion of softer material is herewith achieved at the transition between the aorta and the blood vessel, e.g. the ostium irrespective of the great speed of the blood flow and reactive forces due to the introduction of the balloon catheter or any other catheter.

8 Claims, 2 Drawing Sheets

CATHETER FOR ANGIOPLASTY WITH SOFT CENTERING TIP

The invention relates to a guiding catheter for angioplasty, substantially consisting of a hollow tube (lumen) of flexible torsion-stiff material, onto an end of which connects a tubular extension of flexible material, which is curved according to predetermined varying radii of curvature, and the free end portion of which is provided with a softer material than the flexible material.

The known catheters of the type described in the preamble are used as guiding members during heart catheterization, wherein the relatively wide hollow tube is guided along a previously inserted wire. The tube therefore has to be both flexible and torsion-stiff in order to steer the free end in the aorta and the blood vessels connecting thereto such that the correct entrance, for instance ostium, is found. To this end the tubular extension is also curved according to predetermined radii of curvature in order to be able to reach the correct entrance of the blood vessel. The soft end portion serves to prevent damage to the wall of the aorta or the blood vessel. With the known catheters, holding the end portion in the correct position at the transition between the aorta and the blood vessel, as said ostium, remains a problem because of for instance the great speed of the blood flow and reactive forces due to the introduction of the balloon catheter or any other catheter. While it is true that the curved tubular extension is supported against the wall of the extension, the flexibility of this extension and the soft end portion nevertheless causes a continuously accurate position difficult to maintain.

The invention has for its object to obviate the above mentioned drawback and provides for that purpose a guiding catheter which is distinguished in that the end portion of softer material is provided with at least three radially protruding elements.

These three radially protruding elements ensure a a-traumatic centering of the soft end portion in the blood vessel in particular said ostium, whereby this end portion remains better in position, while due to the distance creating working the free passage of the blood is hardly or not at all obstructed. It is necessary that a continuous blood flow has to be maintained around the catheter in order to supply blood to the heart vessels.

In a preferred embodiment the radially protruding elements are embodied as ridge-shaped parts extending in axial direction of the catheter, preferably having an arc-like outer curvature seen in tangential direction. A very great stability of the end portion of softer material is herewith achieved.

According to a further development of the invention it is recommended to support the inside of the end portion of softer material by a narrowed tubular portion of the extension, whereby the lengthwise stability of the end portion is improved.

In order to further the pliability of the protruding elements or ridge-shaped parts in inward sense, it is advantageous according to the invention to embody this narrowed tubular portion of the extension with passages at the location of the protruding elements.

Due to these passages the protruding elements can be pressed inward; so insertion of the catheter through a punction sheath, according the Seldinger technique is still possible, without enlarging the inner diameter of the punction sheath.

Figure 2:
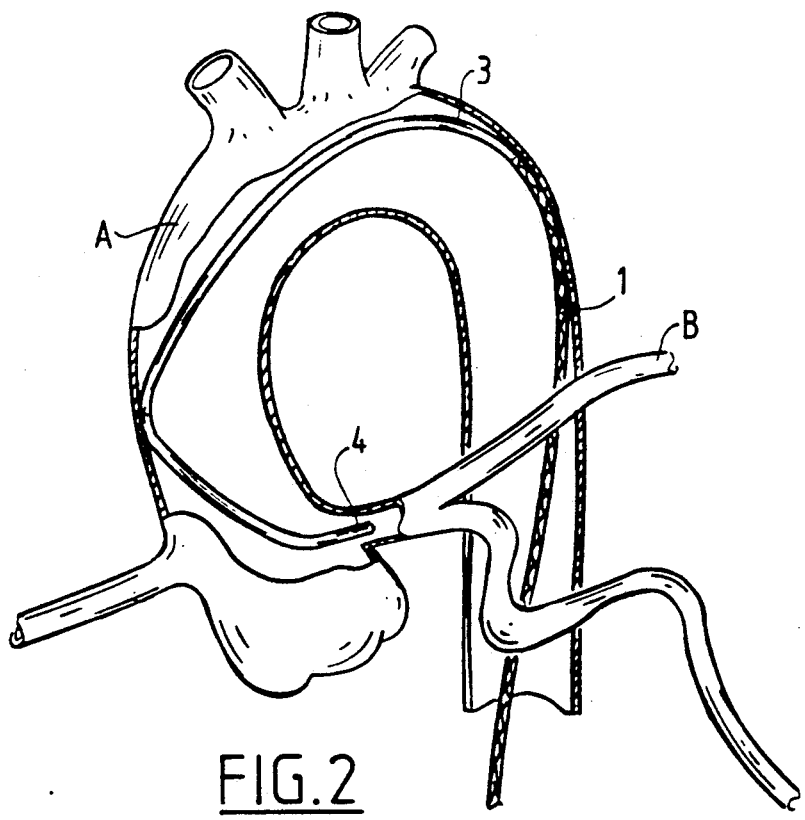
Figure 3:
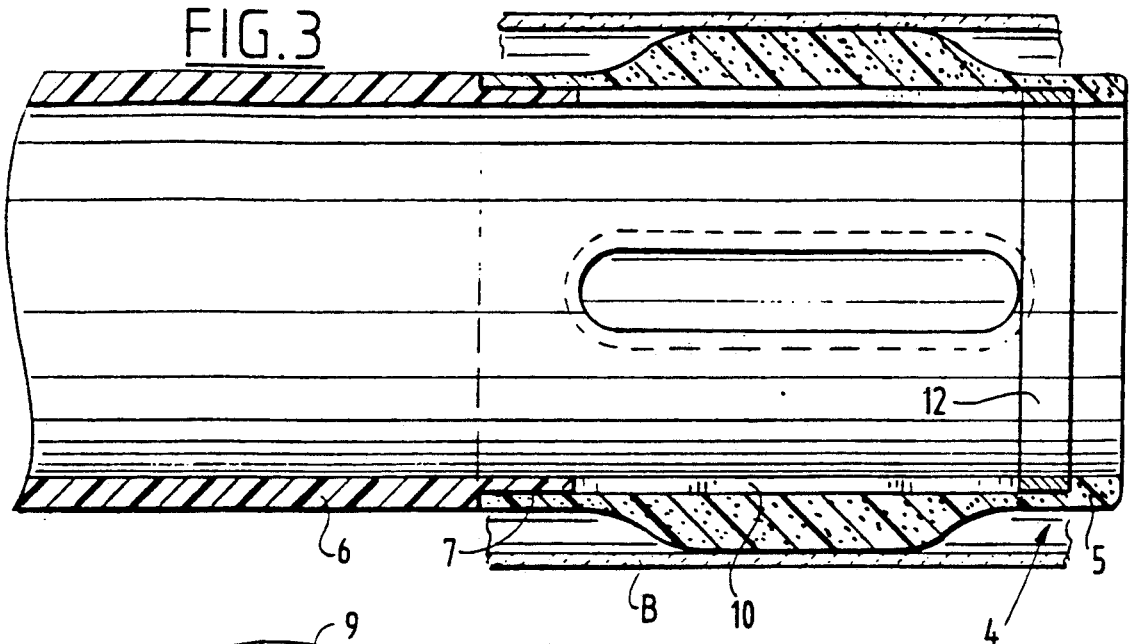
Figure 4:
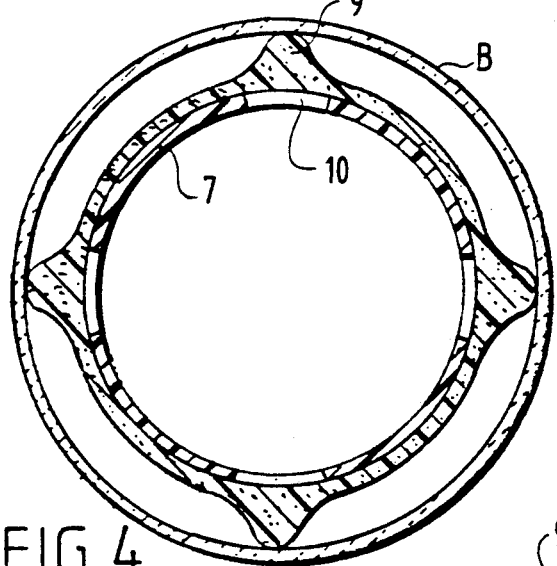
Figure 6:
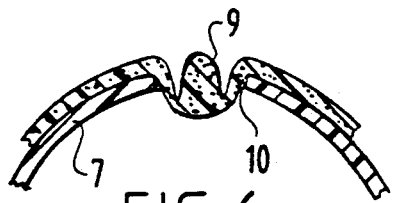
Figure 5:
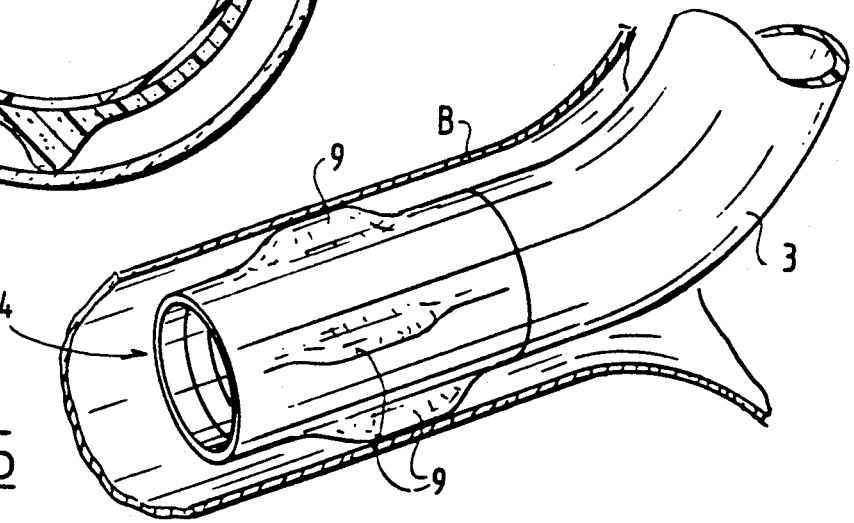
Figure 7:
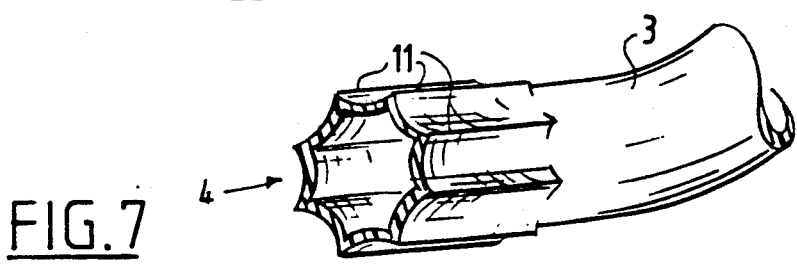

Above mentioned and other features of the invention will be further elucidated in the figure description hereinafter of a number of embodiments. In the drawing:

FIG. 1 shows a perspective view of a patient provided with a catheter according to the invention, FIG. 2 shows a large detail of the aorta with a catheter according to the invention arranged therein, FIG. 3 and FIG. 4 show respectively a lengthwise and a transverse section of the extremity of the catheter from FIG. 2 according to a first embodiment, FIG. 5 shows a perspective view of the centering of the embodiment of FIG. 3 in a blood vessel according to a perspective view, FIG. 6 is a detail of the wall of the end portion of the catheter from FIG. 3 in a different position of the protruding element, FIG. 7 shows a perspective view, corresponding with that of FIG. 5, of an alternative embodiment of the end portion of the catheter according to the invention.

The catheter shown in the figures consists of a hollow tube 1 of flexible torsion-stiff material, which at the end 3 remote from the hand grip 2 is extended with a tubular curved portion, the bends of which each display an adapted radius of curvature, see FIG. 2. This curved extended portion 3 is such that it is adapted to the curvature of the aorta A, whereby it is possible to place the end portion of the extended portion 3 at the entrance of a blood vessel B connecting onto the aorta A. The curved end portion 3 is carried via an artery in the arm of the patient from FIG. 1 to the aorta, by pushing it up and rotating it such that the positioning at the entrance of the blood vessel B can take place. Therein the curve of the tubular part 1 as well as that of portion 3 supports against the side wall of the aorta. This method of positioning is however still not sufficient to position the end 4, which is further elucidated hereunder, precisely in the debouchement of the blood vessel, because of the strong flow to which the blood is subjected there and/or the reactive forces of the introduced catheters.

Shown in FIG. 3–6 is a first embodiment of the end portion 4 of the catheter 1 from FIG. 1 and 2. The end portion is substantially formed of a sleeve-like part 5 of soft material, which gives sufficiently as the catheter is pushed through the artery, so that no damage occurs to the wall thereof. The soft material 5 is supported on the inner side by the hollow tubular portion 6 which is more narrowed in circumference at 7.

The soft material of the end portion 5 is thickened radially outward such that ridge-shaped elements 9 are created which display a determined length. The ridge-shaped, radially protruding elements 9 end at a distance from the free end of the end portion 5.

According to a feature of the invention the more narrowed portion 7 of the tubular extension piece 6 is provided with a passage opening 10 close to the radially protruding elements 9, whereby it is possible for the radially protruding element 9 to be able to give inwardly through this opening 10, should this appear to be necessary during the passage of the catheter in a blood vessel or during insertion into a punction sheath, see FIG. 6.

The above mentioned embodiment has the following result.

If the end portion with the protruding elements 9 is carried into the debouchement of the blood vessel B, see FIG. 5, with a correct choice of catheter the outer periphery of the protruding elements 9 will rest against the inner wall of the blood vessel B, whereby the end portion comes to lie accurately centered in the blood vessel B. With this embodiment it is not only possible to accurately centre and position the end portion, but also to ensure the necessary through-flow of blood. The catheter can nevertheless be used for feeding all usual substances and to inject contrast fluid and such like.

FIG. 7 shows an alternative embodiment, wherein the ridge-shaped protrusions are formed by an end portion that is star-shaped in cross section and exhibits a large number of parallel ribs 11 distributed regularly over the periphery.

It is finally noted that past the passage opening 10 in FIG. 3 the end portion 6 can have a ring 12 that is observable with X-rays, whereby the position of the end portion during the operation can be accurately determined.

Such a ring 12 can likewise be used with the end portion 4 in FIG. 7, for which purpose this ring can either be circular or can likewise display a star-shaped form similar to the cross section of the end portion.

Other embodiments are of course possible within the scope of the invention.

The ridge-like rib 9 can for instance be subdivided into more, successive protruding elements, whereby an interrupted ridge results. This can be an advantage for assisting the blood flow.

The narrowed part 7 can extend beyond the soft tip end, as a-traumatic insertion is still possible due to the ridges extending radially.

I claim:

1. A catheter for angioplasty, comprising:
   a hollow tube of flexible torsion-stiff material;
   a tubular extension of flexible material disposed on one end of said hollow tube, wherein said tubular extension is curved according to a predetermined varying radii of curvature and defines an end opening, and wherein a distal end portion of said tubular extension is provided with a softer material than the flexible material; and
   centering means for centering the tubular extension in a blood vessel, said centering means comprising at least three radially protruding noninflatable elements formed of the softer material and extending outwardly from the distal end portion.

2. A catheter as claimed in claim 1, wherein an annular element observable by x-rays is embedded in the distal end portion.

3. A catheter as claimed in claim 1, wherein each said radially protruding element has a ridge-like form.

4. A catheter as claimed in claim 3, wherein each said radially protruding element has an arc-like outer curvature.

5. A catheter as claimed in claim 1, wherein said at least three radially protruding elements extend longitudinally along the tubular extension and end at a predetermined distance from the end opening thereof.

6. A catheter as claimed in claim 5, wherein an annular element observable by x-rays is embedded in the distal end portion between the end of the radially protruding elements and the open end of the tubular extension.

7. A catheter as claimed in claim 1, wherein an inner side of the distal end portion is supported by a narrowed portion of the tubular extension.

8. A catheter as claimed in claim 7, wherein passage openings are provided in the narrowed portion of the tubular extension at locations corresponding to each of said at least three radially protruding elements.

* * * * *